United States Patent
Armstrong et al.

(10) Patent No.: US 6,262,037 B1
(45) Date of Patent: Jul. 17, 2001

(54) **PHARMACEUTICAL COMPOSITIONS FOR THE AMELIORATION OF ENTEROPATHOGENIC *E. COLI* INFECTION**

(76) Inventors: Glen D. Armstrong, 7951 91 Ave., Edmonton (CA), T6C 1P9; Rosa P. Vanmaele, 9015-144 St., Edmonton, Alberta (CA), T5R 0R5

( * ) Notice: Subject to any disclaimer, the term of this patent is extended or adjusted under 35 U.S.C. 154(b) by 0 days.

(21) Appl. No.: 09/058,776

(22) Filed: Apr. 13, 1998

Related U.S. Application Data

(62) Division of application No. 08/679,184, filed on Jul. 12, 1996, now Pat. No. 5,858,698, which is a continuation of application No. 08/230,810, filed on Apr. 21, 1994, now abandoned.

(51) Int. Cl.$^7$ ................................................. A61K 31/715
(52) U.S. Cl. .............................................................. 514/53
(58) Field of Search ................................................. 514/53

(56) References Cited

U.S. PATENT DOCUMENTS 4,851,338 * 7/1989 Mardh et al. ........................... 435/34
5,272,066 * 12/1993 Bergh et al. ........................... 435/97

OTHER PUBLICATIONS

*Biochem & Biophys Res Comm*, 111(2):566 (1983).

Camara, et al., "Inhibition of Enteropathogenic *Escherichia coli* (EPEC) Adhesion to HeLa Cells by Human Colostrum; Detection of Specific sIgA Related to EPEC Outer–Membrane Proteins", *Int Arch Allergy Immun*, 103:307–310 (1994).

Chart and Rowe, "The outer membrane protein of enteropathogenic *Escherichia coli*, described as the 'localised adherence factor' is OmpF and probably not involved in adhesion to Hep–2 cells", *FEMS Microb Let*, 61:291–296 (1989).

Cravioto, et al., "Inhibition of Localized Adhesion of Enteropathogenic *Escherichia coli* to Hep–2 by Immunoglobulin and Oligosaccharide Fractions of Human Colostrum and Breast Milk", *JID*, 1991:163 (Jun.).

*J Chromat*, 212:313–322 (1981).

Liukkonen, et al., *J Biol Chem*, 267(29):21105–21111 (1992).

Parkkennen, et al., *Eur J Biochem*, 136:355–361 (1983).

Scaletsky, et al., "Isolation and Characterization of the Localized Adherence Factor of Enteropathogenic *Escherichia coli*", *Infect Immun*, 56(11):2979–2983 (Nov. 1998).

Vanmaele, et al., *Infect Immun*, 63:191–198 (1991).

HCAPLUS abstract No. 1980:591921 of JP 55–069506, May 26, 1980.*

* cited by examiner

Primary Examiner—Kathleen K. Fonda
(74) Attorney, Agent, or Firm—Burns Doane Swecker & Mathis LLP

(57) ABSTRACT

Therapeutic and diagnostic methods are provided for treatment and detection of enteropathogenic *E. coli* (EPEC) enteric infections. Also provided is an assay for the identification of compositions which are effective inhibitors of EPEC infection.

10 Claims, 5 Drawing Sheets

PHARMACEUTICAL COMPOSITIONS FOR THE AMELIORATION OF ENTEROPATHOGENIC *E. COLI* INFECTION

This application is a divisional of application Ser. No. 08/679,184, filed on Jul. 12, 1996, now U.S. Pat. No. 5,858,698, which is a continuation application of application Ser. No. 08/230,810, filed on Apr. 21, 1994, now abandoned.

BACKGROUND OF THE INVENTION

1. Field of the Invention

This invention relates generally to pathogenic, diarrheagenic *E. coli* and specifically to the diagnosis and treatment of enteropathogenic *E. coli* (EPEC).

2. Description of Related Art

The *Escherichia coli* comprise a heterogenous group of microorganisms with wide ranging potential for interacting with their hosts. There are three broad categories into which the *E. coli* can be subdivided: 1) non-pathogenic *E. coli* which comprise the normal flora of the host; 2) opportunistic pathogen (e.g., uropathogenic *E. coli;* and 3) true pathogens. The diarrheagenic *E. coli* are true pathogens and are further subdivided into at least five or six groups based on defined clinical symptoms and virulence mechanisms. These groups include enteroinvasive (EIEC), enterotoxigenic (ETEC), enterohemmorhagic (EHEC), enteroaggregative (EaggEC), and enteropathogenic (EPEC) and diffuse adhering (DAEC).

The ability of pathogenic bacteria to adhere to host epithelial cells is regarded as a prerequisite for the initial colonization of host tissue (Svanborg-Eden, et al., *Lancet*, ii:490, 1976; Beachey, E., *J. Infect. Dis.* 143:325, 1981; Gaastra and deGraaf, *Microbiol. Rev.* 46:129, 1982). In many cases, the adhesion of *E. coli* and other gram negative bacteria takes place through the binding of bacterial pili to specific receptors on the host cell surface, some of which have been identified as glycolipids and glycoproteins (Anderson, et al., *Infect. Immun.* 29:897, 1980; Sharon and Lis, *Science* 246:227, 1989). The specificity of the bacterial adhesions, on the one hand, and the range of receptor structures expressed by particular epithelial cells, on the otherhand, have been suggested to be important determinants of the host range and tissue tropism of each pathogen.

Enteropathogenic *E. coli* are diarrheagenic serotypes which do not produce heat labile or heat stable enterotoxins. The virulence determinants of enteropathogenic *E. coli* strains have not been defined, but the typical mode of attachment to intestinal cells has implicated that the adherence property is a major virulence (Clausen, et al., *J. Pediatr.* 100:358, 1982). This type of adherence does not appear to be solely mediated by fimbriae (Scotland, et al., *FEMS Microbiol. Lett.* 20:191, 1983). These strains cause characteristic ultrastructural intestinal lesions and electron microscopic examinations of the affected segments show a marked effacement of the microvilli and disorganization of the underlying cytoskeletal elements.

Enteropathogenic *E. coli* strains adhere in vitro to epithelial cells such as HeLa or Hep-2 in characteristic patterns that are classified as localized, diffused and aggregative patterns (Cravioto, et al., *Curr. Microbiol.* 3:95, 1989; Scaletsky, et al., *Infect. Immun.* 45:534, 1984). The strains showing localized adherence (LA) have been more frequently encountered in persistent diarrhea, and their diarrheagenic potential experimentally proven by human volunteer studies (Levine, et al., *J. Infect. Dis.* 152:550, 1985). Localized adherent enteropathogenic *E. coli* strains harbor plasmids of 50–80 MDa called EPEC adhesive factor (EAF) plasmids that have been shown to be involved in the ability to adhere to HeLa or Hep-2 cells (Levine, et al., supra). The epithelial cell surface for interaction with a variety of pathogenic bacteria has been shown to have glycosphingolipids which are a prerequisite for successful colonization. This relationship is best exemplified by the uropathogenic *E. coli* which bind to Gal$\alpha$1–4$\beta$Gal structures in glycosphingolipids and *Neisseria gonorrheae* which recognize the lactosyl portion of the glycolipids.

Although studies of various cell surface interactions between eukaryotic cells and pathogenic bacteria have attempted to identify the ligand/receptor relationships, there is still a need for further identification and characterization of the structures which are specifically bound by enteropathogenic *E. coli* (Jagannatha, H. M., et al., *Microbial Path.*, 11:259–268, 1991 and Rafiee, et al., *J. Cell Biol.*, 115:1021–1029, 1991). This latter understanding is essential to developing effective therapeutic treatment and methods of diagnosis for enteropathogenic *E. coli* mediated diseases. The present invention identifies the nature of the interaction between the enteropathogenic *E. coli* and the epithelial cell and, thereby, provides the basis for a method of ameliorating and diagnosing enteropathogenic *E. coli* enteric infections.

SUMMARY OF THE INVENTION

In a first embodiment, the invention provides a method for ameliorating an enteropathogenic *E. coli* enteric infection in a subject which comprises administering to the subject an effective amount of a composition comprising an isomer of lactosamine or sialyllactosamine.

In another embodiment, the invention provides a method for detecting an enteropathogenic *E. coli* in a sample comprising contacting an isomer of lactosamine, an isomer of sialyllactosamine, or a monolayer of epithelial cells with the sample and detecting binding of the *E. coli* to the isomer or detachment of the monolayer. While HeLa and Hep-2 cells have generally been used in studies of EPEC, the present invention provides an alternative model which utilizes Chinese Hamster Ovary (CHO) cells.

The invention also provides a method for identifying compositions which are effective inhibitors of EPEC enteric infections using the detachment of CHO cell monolayers as a detection method.

DETAILED DESCRIPTION OF THE INVENTION

Figure 1:
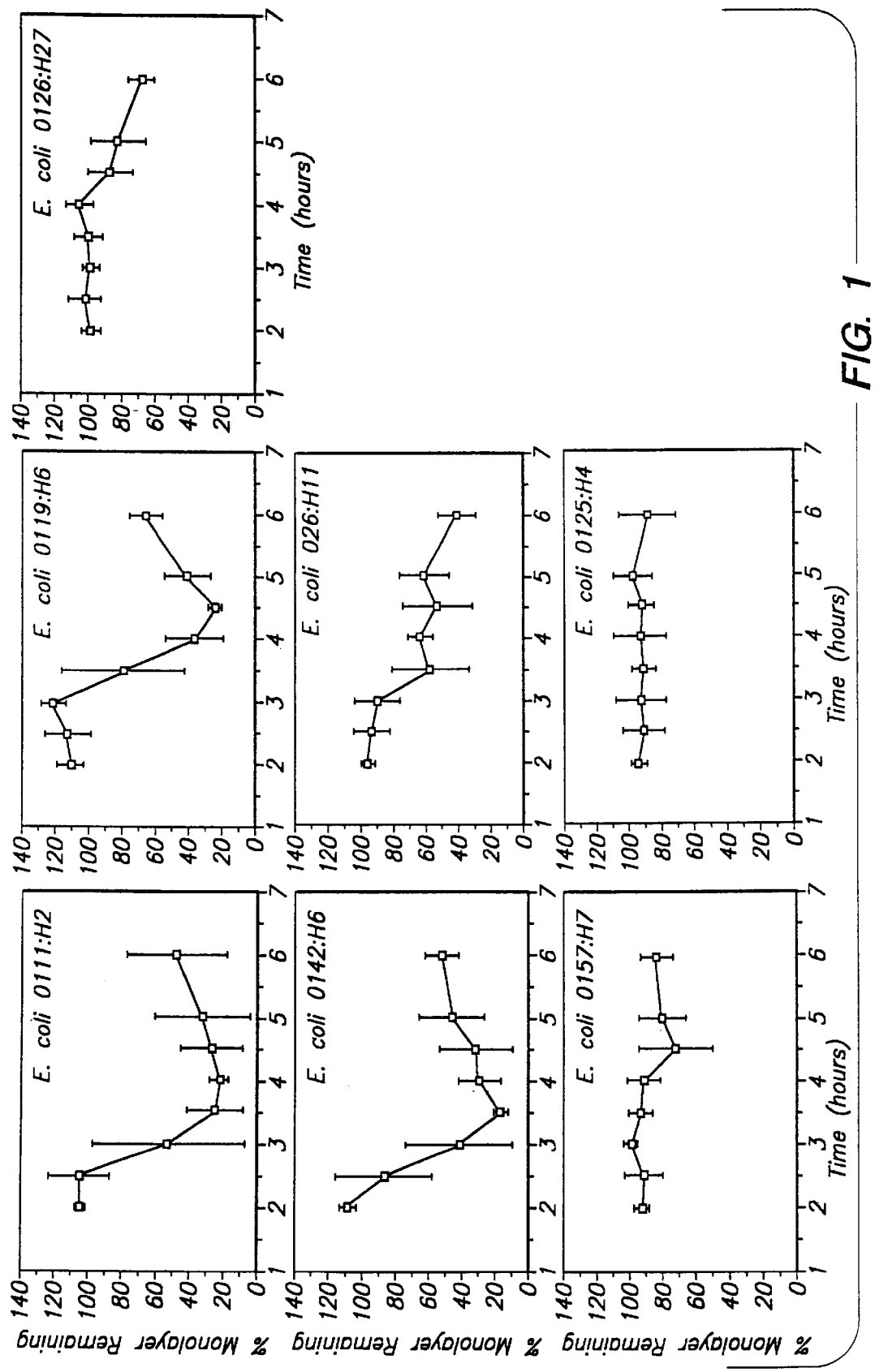
FIG. 1 shows the % monolayer remaining over time (0–6 hours) after treatment of CHO cells with *E. coli* strains 0111:H2, 0142:H6, 0157:H7, 0126:H27, 0119:H6, 026:H11, and 0125:H4.

The present invention is based on the discovery that sialyl and asialo glycans are required in EPEC bacterial attachment and invasion of epithelial cells, such as those of the gastrointestinal tract. The compositions required for attachment and invasion of cells can be used as competitive binding inhibitors for the bacteria, thereby preventing infection of the host cells. The oligosaccharides described in the method of the invention may provide alternative physical surfaces for EPEC colonization and identification and reduce EPEC binding to epithelial cells in the intestines, for example, and provide a vehicle for eliminating the bound EPEC from the body.

In a first embodiment, the invention provides a method for ameliorating an enteropathogenic *E. coli* enteric infection in a subject which comprises administering to the subject a therapeutically effective amount of a composition comprising an isomer of lactosamine or sialyllactosamine or salts thereof. These isomers may comprise multivalent straight or branched disaccharide subunits which are homogeneous or heterogeneous with respect to the various isomers. Examples of preferred lactosamine isomers include βGal(1–3)βGlcNAc and βGal(1–4)βGlcNAc. Examples of preferred sialyllactosamine isomers include αNeu5NAc(2–3)βGal(1–3)βGlcNAc, αNeu5NAc(2–3)βGal(1–4)βGlcNAc, αNeu5NAc(2–6)βGal(1–3) βGlcNAc, and αNeu5NAc(2–6)βGal(1–4)βGlcNAc.

If desired, multiple copies of the isomers can be coupled in close proximity, preferably using a scaffolding provided by a carrier moiety. The multivalency and spacing can be controlled by selection of a suitable carrier moiety. Such moieties include molecular supports which contain a multiplicity of functional groups that can be reacted with functional groups associated with the isomers used according to the invention. A preferred approach involves coupling of the isomers to amino groups of the carrier through reductive amination. Reductive amination is a particularly convenient way to couple aldehyde moieties to free amino groups by first forming the Schliff base and then treating the conjugate with a reducing agent, such as a hydride reducing agent. Typically, the amino group-bearing carrier is mixed with the carbohydrate moiety at about pH 9 and allowed to form the Schiff base; the solvents are typically evaporated and reducing agent is added at high pH to complete the reaction.

Convenient carrier moieties which can be used to obtain multivalent forms of the isomers include proteins and peptides, particularly those containing lysyl residues which have ε-amino groups available for binding. Carriers which are non-digestible and methods for coupling carbohydrates to such carriers are well known to those of ordinary skill in the art. For example, a convenience carrier to obtain a trivalent couple is the peptide Lys-Tyr-Lys. Complete reaction of the isomer with the free amino groups on this peptide result in a trivalent moiety. Carriers can be organic, for example cellulose, or inorganic, for example, glass beads, ceramic material, or silica. Preferably the carrier is non-digestible such that it remains intact and, thereby, can bind with the organism.

A variety of carriers can be used, including proteins such as BSA or HSA, as well as multiplicity of peptides including, for example, pentapeptides, decapeptides, pentadecapeptides, and the like. Preferably, the peptides or proteins contain the desired number of amino acid residues having free amino groups in their side chains; however, other functional groups, such as sulfhydryl groups or hydroxyl groups can also be used to obtain stable linkages. For example, the isomers may be oxidized to contain carboxyl groups at the reducing terminus which can then be derivatized with either free amino groups to form amides or with hydroxyl groups to form esters.

The method of the invention is useful or "ameliorating" an EPEC enteric infection. As used herein, the term "ameliorating" means treating the EPEC infection and symptoms thereof. The term "ameliorate" denotes a lessening of the detrimental effect of the EPEC associated disease in the subject receiving therapy. The method of the invention is useful for ameliorating the disease by administering a lactosamine or sialyllactosamine isomer to inhibit binding of an *E. coli* natural ligand to an epithelial cell receptor.

As used herein, the term "therapeutically effective amount" means that the amount of the pharmaceutically active substance is of sufficient quantity and activity to induce a desired pharmacological effect which, in the present invention, is the inhibition of EPEC binding to an epithelial cell receptor. The amount of substance, can vary greatly according to the effectiveness of a particular active substance, the age, weight, and response of the individual host as well as the nature and severity of the host's symptoms. Accordingly, there is no upper or lower critical limitation upon the amount of the active substance. The required quantity to be employed in the present invention can readily be determined by those skilled in the art without undue experimentation. For example, Armstrong, et al., (*J. Infect. Dis.*, 164:1160–1167, 1991) have shown that 10 ng of oligosaccharide will effectively neutralize shiga-like toxins in vitro. From these data, one skilled in the art could predict an effective dosage of 0.5 μg/kg body weight of oligosaccharide coupled at a rate of 1 μg/g of carrier.

In the method of the invention, the isomer may be coupled to a pharmaceutically acceptable indigestible carrier. In one embodiment, the pharmaceutically acceptable carrier is a controlled release vehicle such as a biodegradable microsphere as described herein. The term "microcapsules" refers to microspheres wherein a pharmaceutically active substance is encapsulated by a coating of coacervates. Specifically useful in the present invention is a solid microsphere which is a matrix type rather than a core-shell type. If the pharmaceutically active substance is a charged molecule, the molecule is likely to participate in the complex coacervation process to form the microsphere wherein the substance is entangled with the microsphere matrix.

As applied in the present invention, the term "pharmaceutically active substance" encompasses any substance that ill produce a therapeutically beneficial pharmacological response when administered to a host, including both humans and animals. In addition to the oligosaccharide, one or more other pharmaceutically active substances may be included, if desired, in a pharmaceutical composition used in the method of the present invention.

Thus, an effective therapeutic composition may comprise the oligosaccharide, the carrier and one or more other pharmaceutically active substances. The term "pharmaceutically active substance" as used herein for the compositions of the invention includes, without limitation, drugs, radioisotopes, immunomodulators, and lectins. Similar substances are within the skill of the art. The drugs with which can be incorporated in the compositions of the invention include compounds which are classically referred to as drugs such as mitomycin C, daunorubicin, vinblastine, AZT, and hormones. Preferred drugs are antibiotics which are bacteriocidal or bacteriostatic for the EPEC. Similar substances are within the skill of the art.

As it applies to the pharmaceutical compositions of the invention, the composition incorporates the oligosaccharide and, if desired, one or more other pharmaceutically active substances which are 1) not bound to the carrier, or 2) bound within the carrier, or 3) pendently bound to the carrier, or 4) bound within the carrier and pendently bound to the carrier. When the oligosaccharide or other pharmaceutically active substance is not bound to the matrix, then it is merely physically dispersed with the carrier. When the oligosaccharide or other pharmaceutically active substance is bound within the carrier it is, for example, part of the backbone. When the oligosaccharide or other pharmaceutically active substance is pendently attached it is chemically linked through, for example, by ionic or covalent bonding, to a side chain of the carrier. In a preferred embodiment, the oligosaccharide is bound to the carrier and one or more other pharmaceutically active substances, such as an antibiotic, are physically dispersed within the carrier such that the antibiotic diffuses out of the carrier.

Alternatively, the additional pharmaceutically active substance can be bound to the oligosaccharide rather than the carrier. Techniques for binding to oligosaccharide are well known to those of ordinary skill in the art.

The pharmaceutically active substance can be employed in the present invention in various forms, such as molecular complexes or pharmaceutically acceptable salts. Representative examples of such salts are succinate, hydrochloride, hydrobromide, sulfate, phosphate, nitrate, borate, acetate, maleate, tartrate, salicylate, metal salts (e.g., alkali or alkaline earth), ammonium or amine salts (e.g., quaternary ammonium) and the like. Furthermore, derivatives of the active substances such as esters, amides, and ethers which have desirable retention and release characteristics, but which are readily hydrolyzed in vivo by physiological pH or enzymes can also be employed.

As used herein with respect to the pharmaceutically active substance, the term "controlled release" means that the present compositions require at least an hour to release a major portion of the active substance into the surrounding medium, e.g., about 1–24 hours or even longer.

The surface of the dispersion system may be modified in a variety of ways. Non-lipid material may be conjugated via a linking group to one or more hydrophobic groups, for example, alkyl chains from about 12–20 carbon atoms. In the case of a synthetic membrane vesicle delivery system, lipid groups can be incorporated into the lipid bilayer in order to maintain the compound in stabile association with the membrane bilayer. Various linking groups can then be used for joining the lipid chains to the compound and are known to those of ordinary skill in the art.

The pharmaceutical microcapsule composition used in the present invention is premised primarily upon components which are found endogenous to the human body, whether natural or synthetic. The present invention thus makes it possible to employ significantly lesser quantities of non-biological materials than generally used in preparing controlled release pharmaceutical compositions. This high level of biocompatibility reflects a decreased level of cytoxicity and immunogenicity.

There are a number of potential advantages to the use of a biodegradable polymer strategy. By varying the composition and size of the oligosaccharide preparations, it is possible to regulate the pharmacokinetics of local oligosaccharide secretion such that a maximal biological effect is achieved. Alternations in the composition and size and shape of preparations may produce more sustained release and will ultimately result in more effective treatment.

The therapeutic mixture of vehicle/oligosaccharide used according to the method of the invention may also be administered to the subject in a delivery system, such as synthetic or natural polymers, in the form of macromolecular complexes, nanocapsules, microspheres, or beads, and lipid-based systems including oil-in-water emulsions, micelles, mixed micelles, and synthetic membrane vesicles. These systems are known collectively as dispersion systems. Typically, the particles comprising the system are about 20 nm–50 $\mu$m in diameter.

Materials used in the preparation of dispersion systems may be sterilizable via filter sterilization, nontoxic, and biodegradable, such as albumin, ethylcellulose, casein, gelatin, lecithin, phospholipids, and soybean oil. Polymeric dispersion systems can be prepared by a process similar to the coacervation of microencapsulation. If desired, the density of the dispersion system can be modified by altering the specific gravity to make the dispersion hyperbaric or hypobaric. For example, the dispersion material can be made more hyperbaric by the addition of iohexol, iodixanol, metrizamide, sucrose, trehalose, glucose, or other biocompatible molecules with high specific gravity.

One type of dispersion system which can be used according to the invention consists of a dispersion of the oligosaccharide in a polymer matrix. The therapeutic agent is released as the polymeric matrix decomposes, or biodegrades, into soluble products which are excreted from the body. Several classes of synthetic polymers, including polyesters (Pitt, et al., in *Controlled Release of Bioactive Materials*, R. Baker, Ed., Academic Press, New York, 1980); polyamides (Sidman, et al., *Journal of Membrane Science*, 7:227, 1979); polyurethanes (Maser, et al., *Journal of Polymer Science, Polymer Symposium*, 66:259, 1979); polyorthoesters (Heller, et al., *Polymer Engineering Science*, 21:727, 1981); and polyanhydrides (Leong, et al., *Biomaterials*, 7:364, 1986) have been studied for this purpose. Considerable research has been done on the polyesters of PLA and PLA/PGA. These polymers are readily available, since they have been used as biodegradable sutures, and they decompose into non-toxic lactic and glycolic acids (see, U.S. Pat. No. 4,578,384; U.S. Pat. No. 4,765,973; incorporated by reference). These are possible as long as the PLA/PLG ratio is adjusted to give a support that will not degrade in the intestine.

Solid polymeric dispersion systems can be synthesized using such polymerization methods as bulk polymerization, interfacial polymerization, solution polymerization, and ring opening polymerization (Odian, G., *Principles of Polymerization*, 2nd ed., John Wiley epithelial Sons, New York, 1981). Using any of these methods, a variety of different synthetic polymers having a broad range of mechanical, chemical, and biodegradable properties are obtained; the differences in properties and characteristics are controlled by varying the parameters of reaction temperatures, reactant concentrations, types of solvent, and reaction time. If desired, the solid polymeric dispersion system can be produced initially as a larger mass which is then ground, or otherwise processed, into particles small enough to maintain a dispersion in the appropriate physiologic buffer (see, for example, U.S. Pat. No. 4,452,025; U.S. Pat. No. 4,389,330; U.S. Pat. No. 4,696,258; incorporated by reference).

The mechanism of release of therapeutic agent from biodegradable slabs, cylinders, and spheres has been described by Hopfenberg (in *Controlled Release Polymeric Formulations*, pp. 26–32, Paul, D. R. and Harris, F. W., Eds., American Chemical Society, Washington, D.C., 1976). A simple expression describing additive release from these devices where release is controlled primarily by matrix degradation is:

$$M_t/M_\infty = 1 - [1 - k_0 t/C_0 a]^n$$

where n=3 for a sphere, n=2 for a cylinder, and n=1 for a slab. The symbol a represents the radius of a sphere or cylinder or the half-thickness of a slab. $M_t$ and $M_\infty$ are the masses of drug release at time t and at infinity, respectively.

Another dispersion system which can be sued according to the invention is a synthetic membrane vesicle. The term "synthetic membrane vesicle" denotes a structure having one or more concentric chambers, commonly known as liposomes.

When phospholipids are dispersed in aqueous media, they swell, hydrate, and spontaneously form multilamellar concentric bilayer vesicles with layers of aqueous media separating the lipid bilayer. Such systems are usually referred to as multilamellar liposomes or multilamellar vesicles (MLVs) and have diameters ranging from about 100 nm to about 4 $\mu$m. When MLV's are sonicated, small unilamellar vesicles (SUVs) with diameters in the range of from about 20 nm to about 50 nm are formed, which contain an aqueous solution in the core of the SUV. The composition of the synthetic membrane vesicle is usually a combination of phospholipids, particularly high-phase-transition-temperature phospholipids, usually in combination with steroids, especially cholesterol. Other phospholipids or other lipids may also be used. (Szoka, et al., *Annual Reviews of Biophysics and Bioengineering*, 9:467, 1980; Deamer, et al., in *Liposomes*, Marcel Dekker, New York, 1983, 27; Hope, et al., *Chem. Phys. Lipids*, 40:89, 1986).

The composition of the invention, comprising a controlled release vehicle containing an oligosaccharide, is preferably administered orally. Oral compositions may be taken in the form of solutions, suspensions, tablets, pills, capsules, sustained release formulas or powders. Any mode of administration is suitable as long as the therapeutic composition is applied to the gastrointestinal tract, directly or indirectly. The correct dosage range will depend on the severity of the infection, the mode of administration, the mode of formulation, for example.

The pharmaceutical compositions formulated for systemic delivery via the oral route of administration, irrespective of the mode of delivery (immediate, sustained, or controlled release) and the design of dosage forms (either solid, dispersion, or liquid), must be developed within the intrinsic characteristics of gastrointestinal (GI) physiology.

Controlled-release drug administration means not only prolongation of the duration of drug delivery, similar to the objective in sustained release and prolonged release, but the term also implies the predictability and reproducibility of drug release kinetics. Oral controlled-release drug delivery is thus a drug delivery system that provides the continuous oral delivery of drugs at predictable and reproducible kinetics for a predetermined period throughout the course of GI transit. Also included are systems that target the delivery of a drug to a specific region within the GI tract for either a local or a systemic action.

An example of one system for delivery of the compositions used in the method of the invention is an osmotic pressure-controlled gastrointestinal delivery system fabricated by encapsulating an osmotic drug core containing an osmotically active drug (or a combination of an osmotically inactive drug with an osmotically active salt, e.g., NaCl) within a semipermeable membrane made from biocompatible polymer, e.g., cellulose acetate. A delivery orifice with a controlled diameter is drilled, using a laser beam, through the coating membrane or controlling the release of drug solutes and capable of maintaining the structural integrity of the gastrointestinal delivery system during the course of drug release.

The external surface of the semipermeable membrane can also be coated with a layer of bioerodible polymer, e.g., enteric coating, to regulate the penetration of gastrointestinal fluid through the semipermeable membrane and target the delivery of a drug to the lower region of the gastrointestinal tract.

Furthermore, the coating membrane of the delivery system can also be constructed from a laminate of two or more semipermeable membranes with differential permeabilities or a laminate of a semipermeable membrane and a microporous membrane (Great Britain Patent No. 1,556,149) to modulate the rate of water influx and so program the range of drug delivery.

Membrane permeation-controlled gastrointestinal delivery systems are also useful in the method of the invention. A microporous membrane permeation-controlled device is prepared by first compressing the crystals (or particles) of water-soluble drug, in combination with appropriate pharmaceutical excipients, into a core tablet and then coating the tablet with a layer of non-GI-erodible polymer, e.g., a copolymer of vinyl chloride and vinyl acetate. The polymer coating contains a small amount of water-soluble pore-forming inorganic agents, e.g., magnesium lauryl sulfate, which create porosity when the tablet comes into contact with gastrointestinal fluid. Alternatively, the core tablet may be coated with a layer of non-GI-erodible thermoplastic polymer, e.g., polyvinyl chloride, which contains a high loading of plasticizer, e.g., dioctyl opthalate.

Another system well known in the art is the gastric fluid-resistant intestine-targeted controlled-release gastrointestinal delivery device. This device, which is designed to release a gastric fluid-labile drug only in the intestinal region at a controlled rate, is prepared by coating a core tablet of the drug with a combination of an intestinal fluid-insoluble polymer, e.g., ethylcellulose and an intestinal fluid-soluble polymer, e.g., methylcellulose (or hydroxymethylcellulose phthalate).

The gel diffusion-controlled gastrointestinal delivery system is fabricated from gel-forming polymers. It can be prepared by first dispersing the therapeutic dose of the isomer in layers of water-soluble carboxymethylcellulose (CMC), sandwiching the drug-loaded CMC layers between layers of cross-linked carboxymethylcellulose (which is water insoluble, but water swellable) and then compressing these layers to form a multilaminated device.

A pH-controlled gastrointestinal delivery system is prepared by first blending an acidic (or basic) drug with one or more buffering agents, e.g., a primary, secondary, or tertiary salt of citric acid, granulating with appropriate pharmaceutical excipients to form small granules, and then coating the granules with a gastrointestinal fluid-permeable film-forming polymer, e.g., cellulose derivatives. Other GI delivery systems, such as ion-exchange-controlled gastrointestinal delivery systems, and hydrodynamic pressure-controlled gastrointestinal delivery systems are known to those of skill in the art.

Typically, the compositions of the invention will contain from less than 1% to about 95% of the isomer, preferably about 10% to about 50%. Preferably, between about 0.1 $\mu$g/kg and 5 $\mu$g/kg body weight will be administered. Most preferably, between about 0.4 $\mu$g/kg body weight to about 0.7 $\mu$g/kg body weight is administered. The frequency of administration will be determined by the care giver based on patient responsiveness. Other effective dosages can be readily determined by one of ordinary skill in the art through routine trails establishing dose response curves.

Preparations for administration are contained in a "pharmaceutically acceptable carrier". Such carriers include sterile aqueous or non-aqueous solutions, suspensions and emulsions which do not cause undue gastrointestinal distress or irritation. Examples of non-aqueous solvents include propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's, or fixed oils. Preservatives and other additives may also be present such as, for example, antimicrobials, antioxidants, chelating agents, and inert gases and the like.

The invention also provides a method of detecting an enteropathogenic *E. coli* in a sample comprising contacting a monolayer of epithelial cells with the sample and detecting detachment of the monolayer. Preferably the epithelial cells are Chinese Hamster Ovary cells (ATCC CCL61). A cell monolayer is maintained on a solid support such as a 24-well tissue culture plate and incubated at 37° C./5% $CO_2$ in a suitable medium such as MEM or F-12. The samples to be tested and appropriate controls are added to the wells and the plates incubated for 2 to 6 hours. The effects of EPEC are visibly apparent in wells to which samples positive for EPEC were added. The results can be quantitated by removing the media, fixing the cells with methanol and staining with Giemsa stain. The absorbance of the contents from each well is recorded using a microtiter plate reader set at a wavelength of 620 nm. The percent monolayer remaining is calculated as: $(A_{620}$ inoculated well$)/(A_{620}$ uninoculated well$)\times 100$. The sample tested may be derived from a host suspected of having an enteropathogenic *E. coli* infection or derived from the external environment, such as a food source. If desired, the sample may be processed and/or concentrated to enrich for bacteria in the sample. Such enrichment techniques are well known in the art.

Alternatively, the presence of an enteropathogenic *E. coli* strain in a sample can be detected by the ability of the strain to bind to an isomer of lactosamine or sialyllactosamine. Preferably, the isomer is bound to a solid substrate to facilitate binding and immobilization of the enteropathogenic *E. coli* to the isomer. When the isomer is bound to a substrate it is preferable to utilize a spacer moiety such as 8-methoxycarbonylactyl (MCO) to derivatize the isomer (Lemieux, et al., *J. Amer. Chem. Soc.,* 97:4076, 1975). Alternative spacer moieties can be used wherein one spacer terminus provides binding to the isomer and the other terminus provides binding to the solid support. Those of ordinary skill in the art will known of such spacer moieties and their appropriateness for complexing a given isomer and substrate.

Enteropathogenic bacteria which bind to a particular isomer can be detected by various techniques known in the art, such as directly or indirectly labelled antibody or using bacterial stains which allow the bacteria to be detected chromatographically or visually by microscopy.

The invention also provides a method for identifying a composition which inhibits an enteropathogenic *E. coli* enteric infection comprising incubating components comprising the composition, an EPEC strain and an epithelial cell, wherein the incubating is carried out under conditions sufficient to allow the components to interact and measuring the effect on the epithelial cell caused by the composition. Using this method, other compositions which are effective for ameliorating an EPEC enteric infection can be identified by in vitro screening methods. For example, a test composition can be added to a monolayer of CHO cells, along with an EPEC strain, and the disruption of the monolayer observed. If the test composition contains oligosaccharides, for example, which are similar to oligosaccharides found on the receptor of the host's epithileal cell, the CHO monolayer will resist detachment. However, if the test composition is not a suitable inhibitor of EPEC attachment and invasion, the monolayer will become detached.

Alternatively, such compositions can be identified by measuring the ability of a composition to inhibit the binding of a known enteropathogenic *E. coli* strain to an isomer of lactosamine or sialyllactosamine by modifying the in vitro detection method described above to allow interaction between the composition and the strain and measuring the decreased binding of the strain to the isomer.

The following examples are intended to further illustrate but not to limit the present invention.

EXAMPLE 1

Materials and Methods

1. Bacteria

The relevant characteristics of all bacterial strains used in this study are listed in Table 1. The *E. coli* strain 0157:H7 was provided by L. Linarez (Provincial Laboratory of Northern Alberta, Edmonton, Canada). *E. coli* serotype 026:H11 (strain H19) was obtained from Dr. S. M. Scotland (Division of Enteric Pathogens, Central Public Health Laboratory, London, U.K.). All bacteria were grown aerobically at 37° C. in tryptic soy broth (TSB, Difco, Detroit, Mich. U.S.A.).

2. Tissue Culture

CHO-K1 (ATCC CCL 61) cells and CHO cell mutants Lec1 (ATCC CRL 1735), Lec2 (ATCC CRL 1736), and Lec8 (ATCC CRL 1737) were obtained from the American Type Culture Collection (Rockville, Md., U.S.A.). The phenotype of the Lec mutants was confirmed using a previously published procedure (Heerze, et al., *Microb. Pathog.,* 11:257–268, 1991). HEp-2 cells were provided by L. Chui (Provincial Laboratory of Northern Alberta, Edmonton, Canada). Unless stated otherwise, all tissue culture cells were grown at 37° C. in an atmosphere containing 5% $CO_2$ and 95% air in medium supplemented with 10% fetal bovine serum (FBS). All reagents for tissue culture were obtained from Gibco (Burlington, Ontario, Canada).

HEp-2 cells were grown in minimal essential medium with Earle's salts (MEM). CHO cells were grown in F-12 Nutrient Mixture (Ham) and Lec1, Lec2, and Lec8 cells were grown in MEM (αMedium). Confluent monolayers were disrupted using a solution consisting of 0.25% trypsin (v/v) in FC buffer (0.14M NaCl, 5.0 mM KCl, 20.0 mM Tris HCl, 5.0 mM Tris Base, 0.5 mM EDTA, pH 7.2). The cells were resuspended in the appropriate medium and $1.25\times10^5$ cells were added to each well of the 24-well tissue culture plates. The plates were incubated at 37° C. for 24 to 72 hours depending on the experiment and cell line. Subconfluent monolayers were used for the FAS test and LA assay while confluent monolayers were used for all other experiments.

3. Bacterial Replication in Tissue Culture Medium

Approximately $2.0\times10^6$ (5–15 µL) TSB-grown, log phase organisms (determined by measuring culture turbidity at 600 nm) were added to 0.5 mL of FBS-supplemented F-12 Nutrient Mixture (Ham) per well in 24-well tissue culture plates in the absence of CHO cells. The number of viable organisms added was confirmed by performing plate counts from serial dilutions of the inocula. After incubation for 3 hours at 37° C. in a $CO_2$ incubator, aliquots were removed from the wells and serial dilutions were again prepared in order to determine the number of viable organisms. Experiments were done in duplicate and repeated twice. Statistical analyses were performed using SYSTAT software (Evanston, Ill. U.S.A.) on a Macintosh IIci computer. The non-parametric Wilcoxon test was used to evaluate the significance of differences between the number of organisms for each strain present after 3 hours incubation.

4. EPEC-Induced Change in Adherent Properties of CHO Cells

Tissue culture plates were prepared as described previously using CHO, Lec1, Lec2, and Lec8 cells. After the monolayers became confluent, the tissue culture medium was replaced with 0.5 mL fresh medium containing 10% FBS and 0.5% D-mannose and approximately $2.0 \times 10^6$ TSB-grown, log phase organisms were added to each well. Experiments were performed in the presence of D-mannose in order to inhibit type 1 pili-mediated bacterial attachment. Following incubation at 37° C., the monolayers were washed 3 times with phosphate buffered (pH 7.2) physiological saline (PBS) to remove non-adherent CHO cells. The CHO cells remaining in each well were fixed for 10 minutes with methanol and then strained with Giemsa stain for 30 minutes. After the monolayers were washed 3 times with water to remove excess stain, the stained cells were lysed with 2% SDS. These solutions of lysed cells were transferred to 96-well microtiter plates and the absorbance of the contents from each well was recorded using a Titertek Multiskan MC microtiter plate reader set at 620 nm. Each experiment was repeated 3 to 5 times. The percent of monolayer remaining was calculated as follows: $A_{620}$ Inoculated well/$A_{620}$ Uninoculated well ×100. At least 4 independent experiments were performed for each strain.

5. Fluorescent Actin Staining (FAS) Test

The FAS test was done as described by (Knutton, et al., Infect. Immun., 57:1290–1298, 1989). Briefly, subconfluent HEp-2 cell monolayers were grown on 12 mm glass coverslips in 24-well plates as described above. Five µl of an overnight bacterial broth culture was then added to each well in the presence of HEPES [N-2-hydroxyethylpiperazine-N'-2-ethanesulfonic acid]-buffered MEM with 2% FBS and 0.5% D-mannose. After incubation at 37° C. in a $CO_2$ incubator for 3 hours, the coverslips were washed 3 times with PBS. The cells were fixed for 20 minutes using 3% formaldehyde followed by another 3 washes with PBS. Next, the formaldehyde-fixed HEp-2 cells were treated with 0.1% Triton X-100 in PBS for 5 minutes in order to permeabilize the cells. The monolayers were washed 3 times with PBS and then treated with 5 µg/mL solution of fluorescein isothiocyanate-conjugated phalloidin (Phalloidin-FITC labelled, Sigma Chemical Company, St. Louis, Mo. U.S.A.) in PBS for 20 minutes to stain actin. After washing 3 times with PBS, the coverslips were mounted in 80% glycerol/PBS and viewed using a fluorescence microscope fitted with a 340–380 nm excitation filter.

When forming the FAS test on CHO, Lec1, Lec2, or Lec8 cells, it was necessary to reduce the co-cultivation time from 3 to 2 hours prior to staining the monolayers with Phalloidin-FITC. Essentially the same procedure was followed for E. coli 026:H11 and 0157:H7 except the bacteria were co-cultivated with CHO cells for a total of 6 hours. At 3 hours of incubation with 026:H11 and 0157:H7 the CHO cell monolayers were washed and fresh medium was added to prevent bacterial overgrowth. F-12 Nutrient Mixture (Ham) or MEM (αMedium) supplemented with 10% FBS and 0.5% D-mannose was used for co-cultivation of EPEC, 026:H11 or 0157:H7 with CHO and Lec cells respectively. The monolayers were then stained with Phalloidin-FITC and observed in the fluorescence microscope as described above.

6. Localized Adherence (LA) Assay

Subconfluent monolayers of CHO, Lec1, Lec2, and Lec8 cells were prepared on 12 mm glass coverslips in 24-well plates as described previously. Following the addition of approximately $1 \times 10^9$ bacterial to each well in the presence of fresh medium containing 10% FBS and 0.5% D-mannose, the plates were incubated for 1.5 hours at 37° C. The monolayers were washed 5 times with PBS to remove non-adherent bacteria, and then fixed and stained with Giemsa stain as described earlier. Excess stain was removed by washing the coverslips 3 times with water. The coverslips were air dried and mounted on glass slides for viewing using the 100× oil immersion objective of a Reichert light microscope. Between 100 to 125 randomly chosen tissue culture cells were observed and only those having 5 or more bacteria attached as a cluster were scored as positive for localized adherence (Vuopio, et al., J. Exp. Med., 174:1167–1177, 1991). Each experiment was repeated three times.

7. EPEC Invasion Assay

Confluence monolayers of CHO and Lec2 cells were prepared as described previously. The tissue culture medium was replaced with 0.5 mL fresh medium containing 10% FBS and 0.5% D-mannose and approximately $2.0 \times 10^6$ TSB-grown, log phase bacteria were added to each well. Following incubation at 37° C. for 1.5 hours, the monolayers were washed 3 times with PBS, and then incubated with gentamycin (100 µg/mL in tissue culture media) for 1 hour at 37° C. in order to kill extracellular bacteria (Francis, et al., J. Infect. Dis., 164:693–703, 1991). After 3 washes with PBS, the CHO cells were lysed by treating them with 200 µl 1% (v/v) Triton X-100 in PBS for 5 minutes at 37° C. The lysed suspensions were then diluted to 1 mL with TSB and the number of intracellular bacteria was determined from serial dilutions of this mixture. These experiments were repeated 5 times.

EXAMPLE 2

Detachment of CHO and Lec Cell Monolayers

Of all the bacteria tested in this assay, only EPEC isolates (0111:H2, 0119:H6, and 0142:H6) caused detachment of CHO cell monolayers within 2 to 4 hours of co-cultivation. FIG. 1 shows the effect of bacteria on the adherent properties of wild-type CHO cells. After incubating the bacteria for various times, CHO cells remaining attached to the tissue culture wells were fixed and strained with Giemsa stain. Stained cells were then lysed with 2% SDS and the $A_{620}$ of these solutions was used to calculate the percent monolayer remaining relative to uninfected monolayers.

Figure 2:
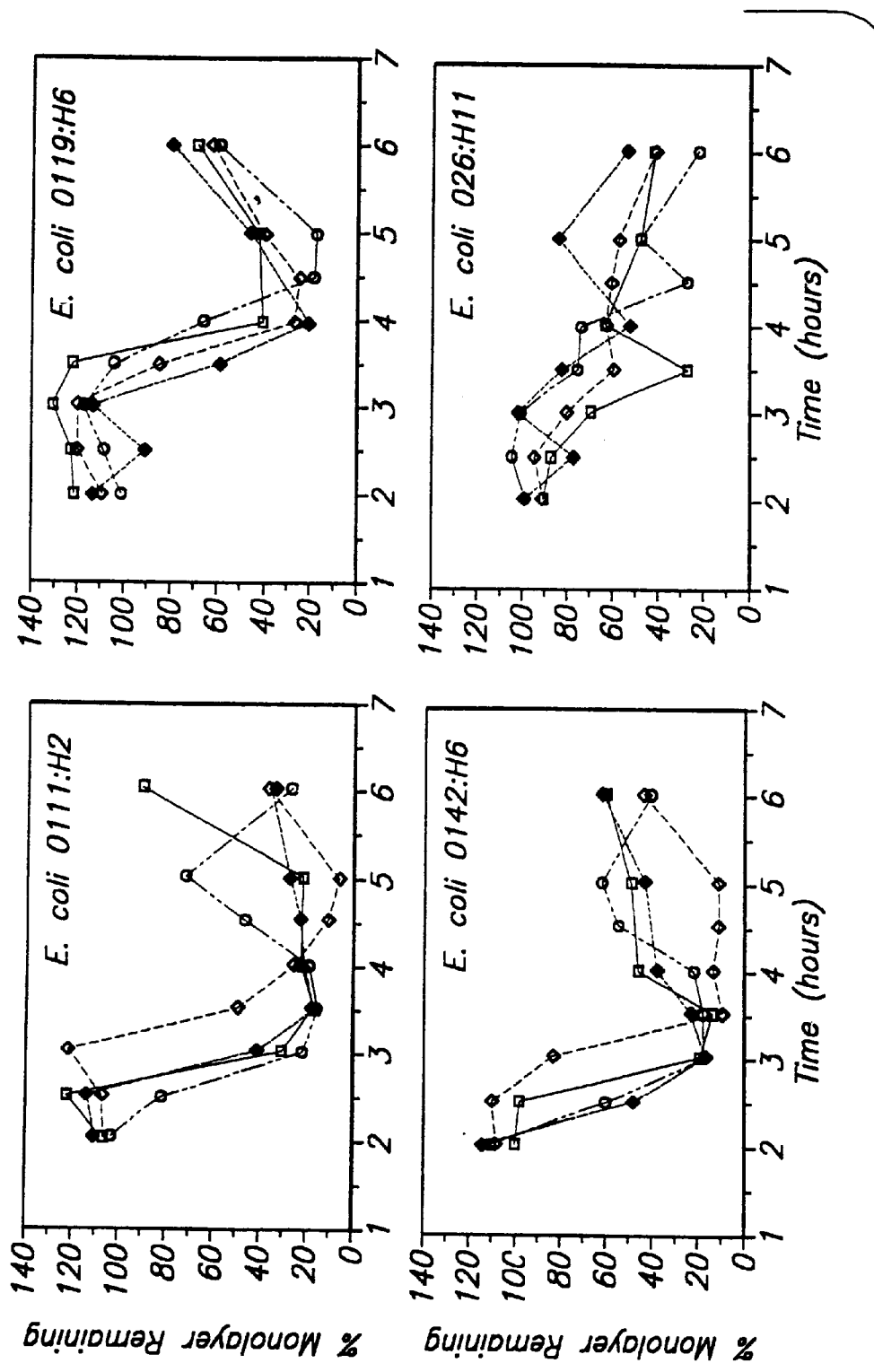
FIG. 2 shows the % monolayer remaining over time (0–6 hours) after treatment of CHO cells with EPEC strains 0111:H2, 0119:H6, and 0142:H6 and non-EPEC strain 026:H11.

The large error bars in this figure were the result of inter-experimental variation in the time (±30 min.) of onset of the effect. However, regardless of the time of onset of monolayer detachment, the rate at which detachment occurred was highly reproducible and was always greater than that observed in CHO cells infected with non-EPEC. FIG. 2 shows the rate of CHO cell monolayer loss caused by EPEC strains (0111:H2, 0119:H6, and 0142:H6) and non-enteropathogenic E. coli 026:H11. Results shown are from independent experiments for each strain.

E. coli 0125:H4 and 0157:H7 caused essentially no detachment of CHO cell monolayers over the 6 hour incubation period whereas E. coli 026:H11 and 0126:H27 caused gradual detachment of the monolayers after 3 to 4 hours incubation. However, the changes in the adherence of CHO cells caused by E. coli 0.126:H27 and 026:H11 were not characteristic of the rapid changes caused by EPEC.

Figure 3:
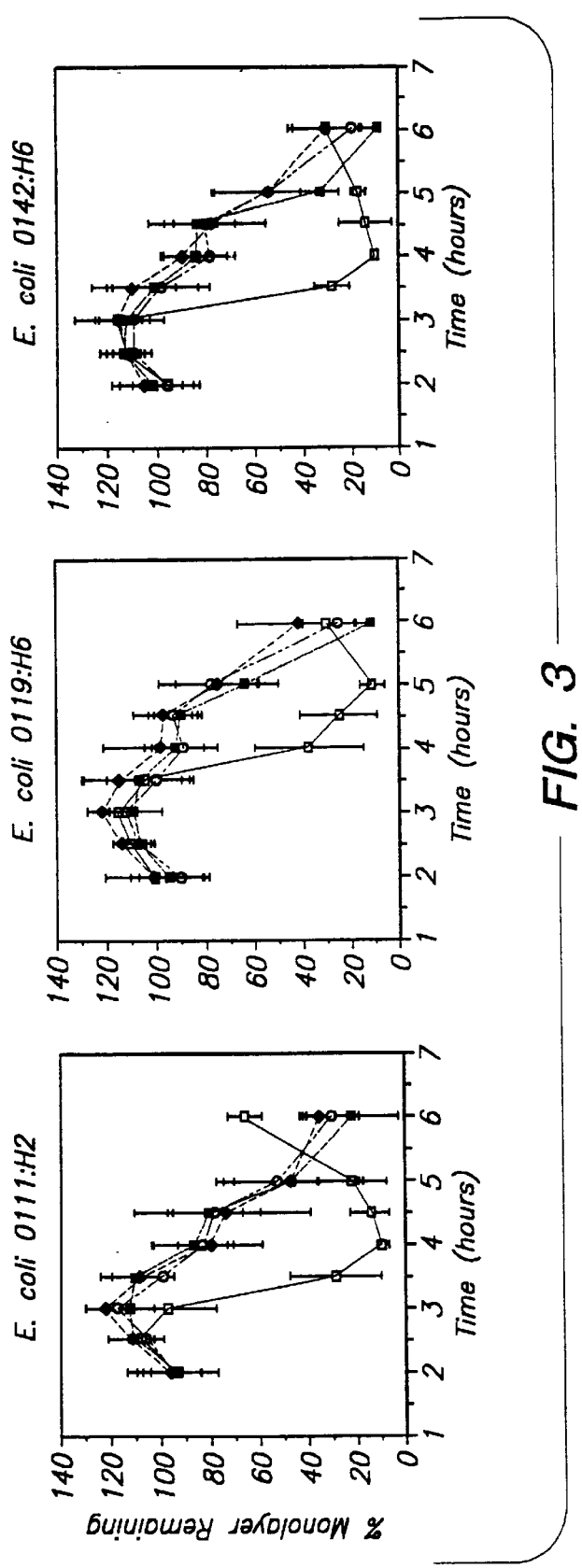
FIG. 3 shows the % monolayer remaining over time (0–6 hours) after treatment of CHO (—□—); Lec1 (—■—); Lec2 (—♦—); and Lec8(---◇---) cell monolayers with *E. coli* 0111:H2, 0119:H6, and 0142:H6.

Lec1 CHO cell mutants lack an N-acetylglucosaminyltransferase (GlcNAc-T1) required for transferring N-acetylglucosamine to α-1,3-linked mannose exclusively in asparagine-linked (N-linked) glycans on cell surface glycoproteins (Stangley, et al., *Proc. Nat'l Acad. Sci. USA*, 72:3323–3327, 1975), Lec2 cells are unable to translocate CMP-sialic acid across Golgi vesicle membranes and are deficient in incorporating sialic acid into glycan sequences on both glycoproteins and glycolipids (Deutscher, et al., *Cell*, 39:295–299, 1984). Lec8 mutants are unable to translocate UDP-galactose into the lumen of the Golgi apparatus and are deficient in galactose incorporation into glycans on glycoproteins and glycolipids (Deutscher, et al., *J. Biol. Chem.*, 261:96–100, 1986). Therefore, Lec8 cells lack terminal sialic acid in addition to galactose (sialic acid acceptors) on glycoprotein and glycolipid oligosaccharide sequences. The rate of EPEC-mediated detachment of Lec1, Lec2, or Lec8 cell monolayers was not as rapid as that observed with wild-type CHO cells. FIG. 3 shows EPEC-induced alteration of CHO (—□—), Lec1 ( ... ■ ... ), Lec2 (—♦—) and Lec8 ( ---◊--- ) cell adherent properties. After the monolayers were incubated with bacteria for various times, the cells remaining attached to the tissue culture wells were fixed and stained using Giemsa stain. Stained monolayers were lysed with 2% SDS and the $A_{620}$ of these solutions was used to calculate the percent monolayer remaining relative to uninfected monolayers.

EXAMPLE 3

Cytotoxins Produced by *E. coli* Strains

There was no detectable production of enterohemolysin or cytolethal distending toxin by the EPEC used in this study (Table 1). Therefore, it is unlikely that production of these soluble factors by EPEC was responsible for the alteration of CHO cell adherent properties. Shiga-like toxins (SLT) were also not responsible for loss of the CHO cell monolayers since neither 0157:H7 nor 026:H11 *E. coli* (both of which produce Shiga-like toxins, Table 1) caused a similar effect.

bacteria in tissue culture medium was determined. Using the non-parametric Wilcoxon test, no significant differences (p>0.07) were detected in the growth of any of the strains in tissue culture medium. Therefore, the loss of the monolayer was not due to more rapid growth of the EPEC.

EXAMPLE 5

Adherence Characteristics of EPEC

Only EPEC, as identified by their positive reaction in the FAS test, caused the rapid detachment of CHO cell monolayers (Table 1). These isolates were found to possess both eae gene and EAF plasmid sequences which may also be used to identify EPEC. Although *E. coli* 026:H11 and 0.157:H7 also possess eae gene sequences, EPEC EAF sequences were not detected. *E. coli* 026:H11 also caused actin accumulation in CHO cells but to a much reduced extent than the classical EPEC. It is not known, therefore, if the inability of *E. coli* 026:H11 to cause a rapid detachment of CHO cell monolayers was the result of lower numbers of adherent bacteria, or if the rapid loss of the monolayers is an effect unique to EPEC. *E. coli* 0157:H7 was FAS negative in our hands because these bacteria failed to adhere to CHO cells.

EXAMPLE 6

EPEC Localized Adherence in Lec Cells

There was no significant difference (p=0.314) in LA of EPEC strains to Lec2 or wild-type CHO cells. This indicated that, although glycan sequences terminating in siliac acid were important for mediating changes in CHO cell adherent properties, LA does not require sialylated glycans (Table 2). However, significantly fewer Lec1 (p=0.008) and Lec8 (p =0.008) cells had localized adherent bacteria. These results suggest lactosamine sequences are required for expression of LA in CHO cells. Moreover, Lec1 mutants, which express altered N-linked glycan but not O-lined glycan or glycolipid sequences, bound significantly more (p=0.011) EPEC than

TABLE 1

Characteristics of *E. coli* Strains

| *E. coli* Strain | Entero-[a] hemolysin | Shiga-like[b] Toxin | Cytolethal[c] Distending Toxin | Rapid Loss of CHD Cell Monolayers | FAS Test CHO | HEp-2 | eae Gene[d] | EAF Plasmid[e] |
|---|---|---|---|---|---|---|---|---|
| 0111:H2 | − | − | − | + | + | + | + | + |
| 0119:H6 | − | − | − | + | + | + | + | + |
| 0125:H4 | − | − | − | − | − | − | − | ND[f] |
| 0126:H27 | − | − | − | − | − | − | − | ND |
| 0142:H6 | − | − | − | + | + | + | + | + |
| 0157:H7 | + | SLTII/SLTI | − | − | ND | ND | + | − |
| 026:H11 | + | SLTI | − | − | + | ND | + | − |

[a]Determined by method of Beutin, et al., Zentralbl. Bakteriol. Mikrobiol. Hyg.A., 267:576–588, 1988).
[b]Determined by method of Armstrong, et al., J. Infect. Dis., 164:1160–1167, 1991); Shiga-like toxin I(SLTI); Shiga-like toxin II(SLTII).
[c]Determined by method of Johnson, et al., FEMS Microbiol. Lett., 43:19–23, 1987).
[d]Determined by method of Louie, et al., Abstr. 92nd Gen. Meet. Am. Soc. Microbiol. American Society for Microbiololgy, pg. 118.
[e]Determined by method of Mass, et al., J. Clin. Microbiol., 28:2842–2844, 1990.
[f]ND - no data.

EXAMPLE 4

Bacterial Replication in Tissue Culture Medium

To determine if the loss of the CHO cell monolayers was due to more rapid replication of the EPEC, the growth of did Lec8 cells which have defects in both glycoprotein and glycolipid sequences. Therefore, lactosamine sequences in both glycoproteins and glycolipids appear to play a role in LA of EPEC to CHO cells.

TABLE 2

Percent CHO and Lec Cell Mutants with Localized Adherent EPEC

| E. coli Strain | CHO | Lec1 | Lec2 | Lec8 |
|---|---|---|---|---|
| 0111:H2 | 86.2 ± 3.6 | 15.6 ± 11.7 | 91.5 ± 11.7 | 9.6 ± 5.6 |
| 0119:H6 | 89.1 ± 4.8 | 17.7 ± 12.4 | 88.4 ± 2.7 | 4.4 ± 1.9 |
| 0142:H6 | 88.7 ± 1.8 | 15.5 ± 10.9 | 89.1 ± 4.6 | 5.7 ± 3.5 |

[a]Mean ± standard deviatian of three independent experiments.

EXAMPLE 7

EPEC Interaction with CHO and Lec2 Cells

Figures 4A, 4B, 4C, 4D:
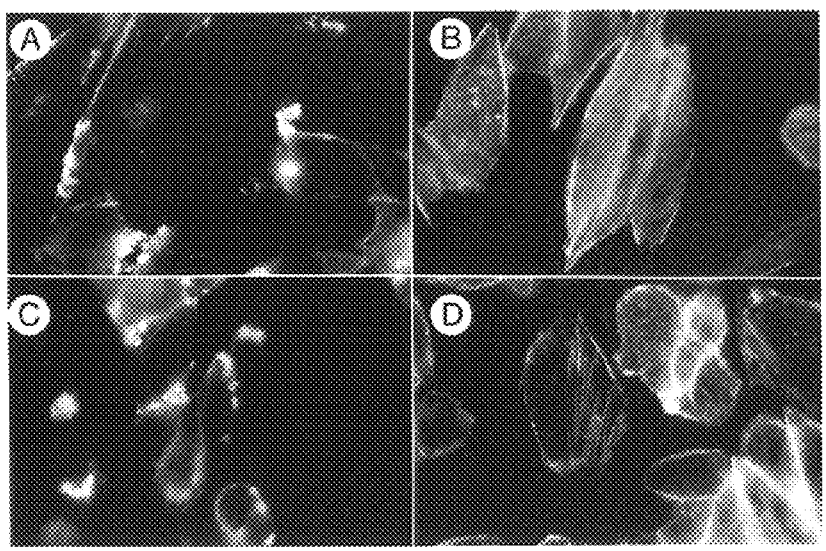
FIGS. 4A–4D show *E. coli* 0119:H6-induced actin accumulation in CHO cells, 4A; Lec1 cells, 4B; Lec2 cells, 4C; and Lec8 cells, 4D.

Actin accumulation caused by *E. coli* 0119:H6 was similar in CHO cells and Lec2 cells. FIG. 4 shows *E. coli* 0119:H6-induced actin accumulation in (A) CHO, (B) Lec1, (C) Lec2, and (D) Lec8 cells. After *E. coli* 0119:H6 was incubated with tissue culture monolayers in the presence of 0.5% D-mannose for 2 hours, the cells were permeabilized using 0.1% Triton X-100, and then stained using FITC-conjugated phalloidin. Monolayers were viewed using a fluorescent microscope in order to detect actin accumulation in tissue culture cells.

Figure 5:
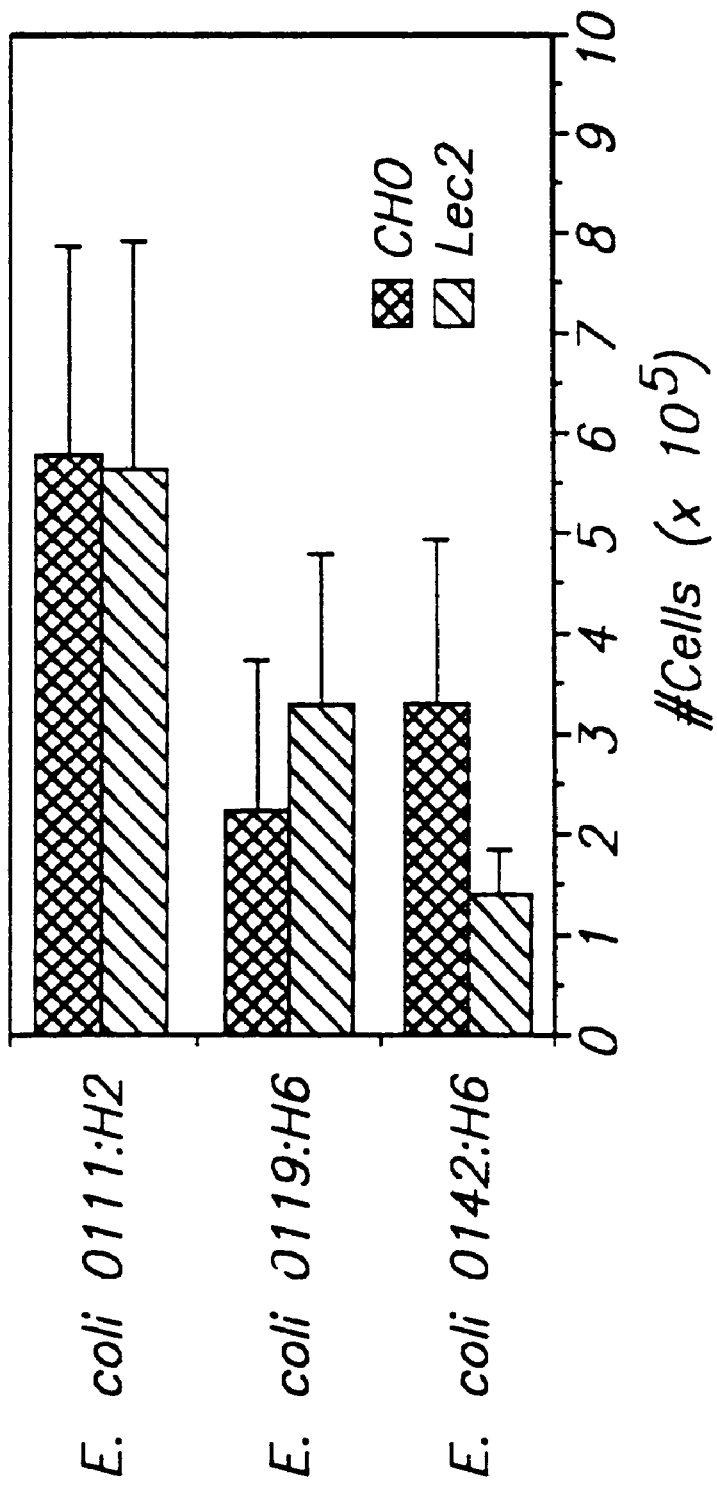
FIG. 5 shows the number of EPEC which invade CHO or Lec2 cells.

Comparable results were seen using EPEC 0111:H2 and 0.142:H6. These results suggest that sialic acid residues in glycoproteins or glycolipids on CHO cells are not required for EPEC-induced actin accumulation in these cells. EPEC-induced actin accumulation in Lec1 or Lec8 cells was not observed, probably resulting from the poor attachment of the bacteria to these cells. Further, there was no significant difference in the ability of *E. coli* 0111:H2 (p=0.715), 0.119:H6 (p=0.225), or 0.142:H6 (p=0.144) to invade CHO or Lec2 cells. FIG. 5 shows EPEC invasion into CHO and Lec2 cells. Following incubation of *E. coli* strains 0111:H2, 0119:H6, and 0142:H6 with CHO or Lec2 cells for 1.5 hours in the presence of 0.5% D-mannose, the monolayers were incubated with gentamycin for 1 hour, and then lysed using 1% Triton X-100. Lysed cell suspensions were diluted in TSB and serial dilutions were performed to determine the number of invasive bacteria.

Therefore, sialic acid residues also do not appear to play a major role in EPEC invasion of CHO cells.

Results previously described by Rafiee, et al., (*J. Cell Biol.*, 115:1021–1029, 1991) demonstrated that AF/R1 pili of RDEC-1, an enteropathogenic *E. coli* of rabbits, bind to sialated glycoprotein complexes in rabbit ileal microvillus membranes. Lec1 cells, which were used in our experiments, lack N-acetylgluocosaminyltransferase (GlcNAc-T1) activity which results in the expression of oligosaccharide structures terminating in mannose on the surface of these cells (Stanley, et al., *Proc. Nat'l Acad. Sci USA*, 72:3323–3327, 1975). O-linked oligosaccharides and glycolipids in this mutant are the same as those present in wild-type CHO cells. In our experiments, the significant reduction in the number of Lec1 cells having locally adherent EPEC suggested that sialyllactosamine in glycoprotein sequences on CHO cells are important for the initial bundle-forming pili-mediated attachment of EPEC (Giron, et al., *Science*, 254:710–713, 1991) (Table 2). However, no significant difference was observed between EPEC LA to wild-type or Lec2 CHO cell mutants, which are deficient only in sialic acid incorporation into glycoproteins and glycolipids (Deutscher, et al., *Cell*, 39:295–299, 1984). Therefore, in contrast to the findings of Rafiee, et al., using rabbit EPEC, the present data suggest sialic acid groups are not required for localized adherence of human EPEC in CHO cells.

The role of sialate sequences in signal transduction processes following intimate attachment by EPEC was examined using CHO and Lec2 cell mutants. There was no observable difference in actin accumulation caused by any of the three EPEC strains (0111:H2, 0119:H6, and 0142:H6) in either CHO or Lec2 cells. Further, there were no significant differences in the numbers of EPEC which invaded CHO or Lec2 cells. Therefore, signal transduction processes associated with EPEC attachment and invasion (i.e. intracellular calcium mobilization and protein phosphorylation) were not apparently affected in Lec2 cells.

The results presented suggest cell surface glycan sequences terminating in sialic acid may be important for the functional expression of EPEC products involved in altering CHO cell adhesive properties.

The foregoing is meant to illustrate, but not to limit, the scope of the invention. Indeed, those of ordinary skill in the art can readily envision and produce further embodiments, based on the teachings herein, without undue experimentation.

What is claimed is:

1. A pharmaceutical composition useful for ameliorating an enteropathogenic *E. coli* enteric infection by reducing binding of enteropathogenic *E. coli* to epithelial cells in an intestine, which comprises a therapeutically effective amount of βGal(1–3)βGlcNAc in combination with a pharmaceutically acceptable excipient and a delivery system which permits delivery of the βGal(1–3)βGlcNAc to the intestine, wherein the delivery system is selected from the group consisting of an osmotic pressure-controlled gastrointestinal delivery system, a membrane permeation-controlled gastrointestinal delivery system, a gel diffusion-controlled gastrointestinal delivery system, a pH-controlled gastrointestinal delivery system, an ion-exchange-controlled gastrointestinal delivery system, and a hydrodynamic pressure-controlled gastrointestinal delivery system.

2. The pharmaceutical composition of claim 1, wherein the βGal(1–3)βGlcNAc is coupled to a pharmaceutically acceptable carrier.

3. The pharmaceutical composition of claim 1, wherein the composition further comprises a second pharmaceutically active substance.

4. The pharmaceutical composition of claim 3, wherein the substance is an antibiotic.

5. The pharmaceutical composition of claim 3, wherein the pharmaceutically active substance is coupled to a pharmaceutically acceptable carrier.

6. A pharmaceutical composition useful for ameliorating an enteropathogenic *E. coli* enteric infection by reducing binding of enteropathogenic *E. coli* to epithelial cells in an intestine, comprising a therapeutically effective amount of βGal(1–4)βGlcNAc in combination with a pharmaceutically acceptable excipient and a delivery system which permits delivery of the βGal(1–4)βGlcNAc to the intestine, wherein the delivery system is selected from the group consisting of an osmotic pressure-controlled gastrointestinal delivery system, a membrane permeation-controlled gastrointestinal delivery system, a gel diffusion-controlled gastrointestinal delivery system, a pH-controlled gastrointestinal delivery system, an ion-exchange-controlled gastrointestinal delivery system, and a hydrodynamic pressure-controlled gastrointestinal delivery system.

7. The pharmaceutical composition of claim 6, wherein the βGal(1–4)βGlcNAc is coupled to a pharmaceutically acceptable carrier.

8. The pharmaceutical composition of claim 6, wherein the composition further comprises a second pharmaceutically active substance.

9. The pharmaceutical composition of claim 8, wherein the substance is an antibiotic.

10. The pharmaceutical composition of claim 8, wherein the pharmaceutically active substance is coupled to a pharmaceutically acceptable carrier.

* * * * *